United States Patent [19]

Nowak

[11] Patent Number: 5,738,518
[45] Date of Patent: Apr. 14, 1998

[54] METHOD OF PRODUCING A DENTAL MODEL AS WELL AS A FASTENING ELEMENT, A MODEL BASEPLATE, A POSITIONING PLATE AND FASTENING SYSTEMS TO CARRY OUT THE METHOD

[76] Inventor: Claude Nowak, Dorfstrasse 30d, CH-5430 Wettingen, Switzerland

[21] Appl. No.: 657,876

[22] Filed: May 31, 1996

[30] Foreign Application Priority Data

Jun. 2, 1995 [CH] Switzerland ............... 1620/95

[51] Int. Cl.⁶ ............... A61C 19/00; A61C 9/00
[52] U.S. Cl. ............... 433/74; 433/213
[58] Field of Search ............... 433/74, 34, 213, 433/14; 24/67.9, 499

[56] References Cited

U.S. PATENT DOCUMENTS

| | | | |
|---|---|---|---|
| 3,404,435 | 10/1968 | Freundlich | 24/67.9 |
| 3,914,007 | 10/1975 | Seidler | 24/67.9 |
| 3,931,677 | 1/1976 | Tinder | 433/74 |
| 3,937,773 | 2/1976 | Huffman | 433/213 |
| 4,139,943 | 2/1979 | Dragan | 433/74 |
| 4,449,931 | 5/1984 | Saito | 433/34 |
| 5,129,822 | 7/1992 | Dobbs | 433/34 |
| 5,197,874 | 3/1993 | Silva et al. | 433/74 |
| 5,363,538 | 11/1994 | Arrendiell et al. | 24/499 |

FOREIGN PATENT DOCUMENTS

| | | | |
|---|---|---|---|
| 528 335 | 2/1993 | European Pat. Off. | |
| 1264683 | 3/1968 | Germany | 433/74 |
| WO 93/11718 | 6/1993 | WIPO | |
| WO 93/24073 | 12/1993 | WIPO | |
| WO 95/26166 | 10/1995 | WIPO | |

Primary Examiner—Cary E. O'Connor

[57] ABSTRACT

A model baseplate made of plastic for producing a dental working model has cutouts for receiving fastening elements, each having two recess-like bearing regions which are located opposite one another transversely to the direction of the maxillary arch, extend away from one another from the bottom towards the top, and are in each case bounded laterally by two bearing faces which extend away from one another towards the center of the cutout. The fastening elements, produced in one piece from stainless steel, each have two rigid limbs which are connected so as to be elastically pivotable by means of an intermediate piece, attached respectively at a distance from their ends, and have contact regions with contact faces on the outer sides for contact with the bearing regions. The limbs extend away from one another from the bottom towards the top corresponding to the bearing regions and enclose an angle of about 10°. During production of the working model, they are fixed in their mutual position so as to be non-pivotable by means of molding compound.

25 Claims, 4 Drawing Sheets

5,738,518

METHOD OF PRODUCING A DENTAL MODEL AS WELL AS A FASTENING ELEMENT, A MODEL BASEPLATE, A POSITIONING PLATE AND FASTENING SYSTEMS TO CARRY OUT THE METHOD

BACKGROUND OF THE INVENTION

1. Field of the Invention

The invention relates to a method of producing a dental model and to a fastening element, a model baseplate, a positioning plate and fastening systems to carry out the method.

Various methods of the generic type for producing dental models, so-called saw-cut models, have been known for a long time, all of which methods, however, either do not fulfill high precision requirements or are complex and expensive because various components required to carry them out cannot be reused or only to a limited extent.

2. Description of the Related Art

A method of this type is mentioned in WO-A-93/24 073, in which a fastening element has two limbs pointing downwards from a support, one of which is elastically deformable. The model baseplate is provided with cutouts for the fastening elements, which cutouts widen towards the bottom so that the fastening elements can be snapped into them. However, a system of this type is unable to fulfill higher requirements with regard to the precision of the positioning of the fastening elements. In particular, the reproducibility of the position of the fastening elements during removal and reinsertion is unsatisfactory. Moreover, insertion and removal are comparatively uncomfortable.

EP-A-0 528 335 relates to a further method of the generic type, in which dagger-like fastening elements made of metal are inserted into funnel-shaped cutouts in a model baseplate made of hot-moldable material after they or the plate have been heated to the molding temperature thereof. In this case, lateral arms of the fastening elements which penetrate slightly into the upper side of the model baseplate serve as depth stops during insertion. Apart from the fact that the fastening elements may possibly not be anchored sufficiently firmly and precisely in the model baseplate, the model baseplate is permanently deformed in this solution, which places restrictions on its reusability.

The invention is based on the object of specifying a method of the generic type, which permits the production of highly precise dental models, in particular a precise reproducibility of the position of parts of the model, supported by one or more fastening elements, on the model baseplate. Moreover, the model baseplate should be able to be reused essentially without restrictions.

Furthermore, particularly suitable components are to be provided by the invention to carry out the method, in particular a suitable fastening element, a suitable model baseplate and a positioning plate which facilitates the execution of the method. Moreover, fastening systems comprising such components are specified, in which the latter are matched to one another in a particularly favorable manner.

This object is achieved by the invention, as characterized in the claims. The method specified permits the use of fastening elements which, for example, to compensate for manufacturing tolerances, are able to adapt to a limited extent to the cutout in the model baseplate when being inserted into the latter, but are fixed in the finished model. In this way, a precise, reproducible insertion into the model baseplate can be guaranteed. Removal and insertion of the model parts can be carried out easily and with little effort.

The fastening element according to the invention provides the mentioned possibility of adaptation to the given shape of the cutout with a sufficiently precise seat therein.

The model baseplate according to the invention guarantees a precise, readily reproducible seat of the fastening element.

Finally, the positioning plate according to the invention substantially facilitates the execution of the method according to the invention.

In the fastening systems specified, the individual components are matched to one another in a particularly favorable manner.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

SUMMARY OF THE INVENTION

Figure 1:
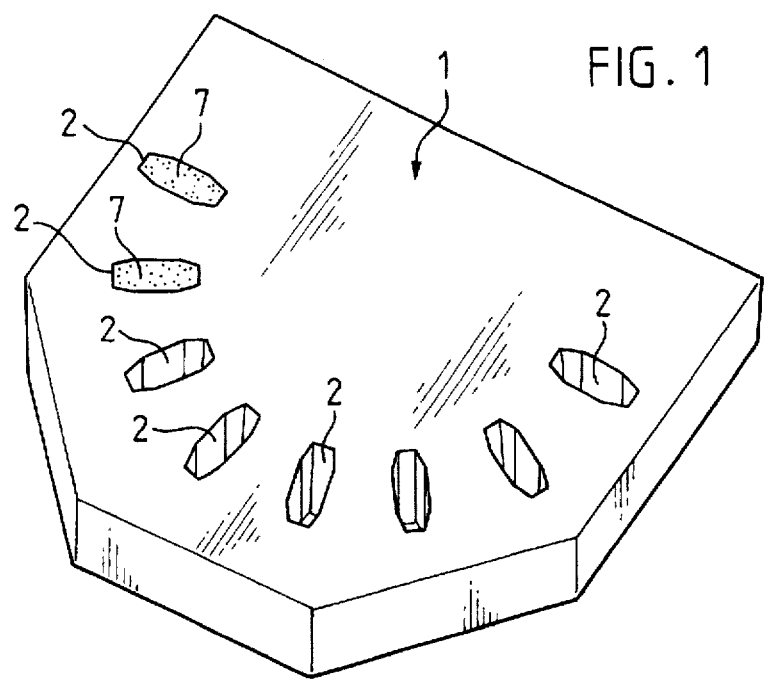
FIG. 1 shows an oblique plan view of a model baseplate.

Additional features and advantages of the invention will be set forth in the description which follows, and in part will be apparent from the description, or may be learned by practice of the invention. The objectives and other advantages of the invention will be realized and attained by the method particularly pointed out in the written description and claims hereof, as well as the appended drawings.

To achieve these and other advantages, and in accordance with the purpose of the invention as embodied and broadly described, the invention is a method of producing a dental working model, in which an impression of a jaw or part of a jaw is made; the impression is filled with molding compound; fastening elements are arranged so as to be removable in a model baseplate; the model baseplate is pressed onto the molding compound so that the fastening elements respectively penetrate at least partially into the molding compound; the molding compound is hardened to form a working model; the working model is separated from the impression and is released from the model baseplate; characterized in that the fastening elements respectively comprise at least two parts which are movable relative to one another, and in that both parts of each fastening element are embedded so far in the molding compound that their mutual position is fixed after hardening of the molding compound.

In another aspect, the invention includes a fastening system for producing a dental working model having a model baseplate with cutouts; and at least one fastening element having at least two limbs and bearing regions for releasable insertion into a cutout in the model baseplate, characterized in that the angle between the limbs of the fastening element and the angle between the bearing regions of the cutout correspond to one another respectively.

In yet another aspect, the invention includes a fastening system for producing a dental working model having a model baseplate and at least one fastening element for releasable insertion into the model baseplate, characterized in that the mutual position of the bearing faces of a bearing region correspond to the mutual position of the contact faces of a limb respectively.

In yet another aspect, the invention includes a fastening system characterized in that the angle between the bearing faces is matched to the coefficient of friction between the materials of the model baseplate and of the fastening element in such a way that self-locking occurs.

In yet mother aspect, the invention includes a fastening system to produce a dental working model having a model baseplate and at least one fastening element for releasable insertion into a cutout in the model baseplate and having a positioning plate, characterized in that the positions of the notches on the bow of the positioning plate correspond to those of the cutouts in the model baseplate.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate one embodiment of the invention and, together with the description, serve to explain the principles of the invention.

DETAILED DESCRIPTION OF THE PREFERRED EMBODIMENTS

Figure 2:
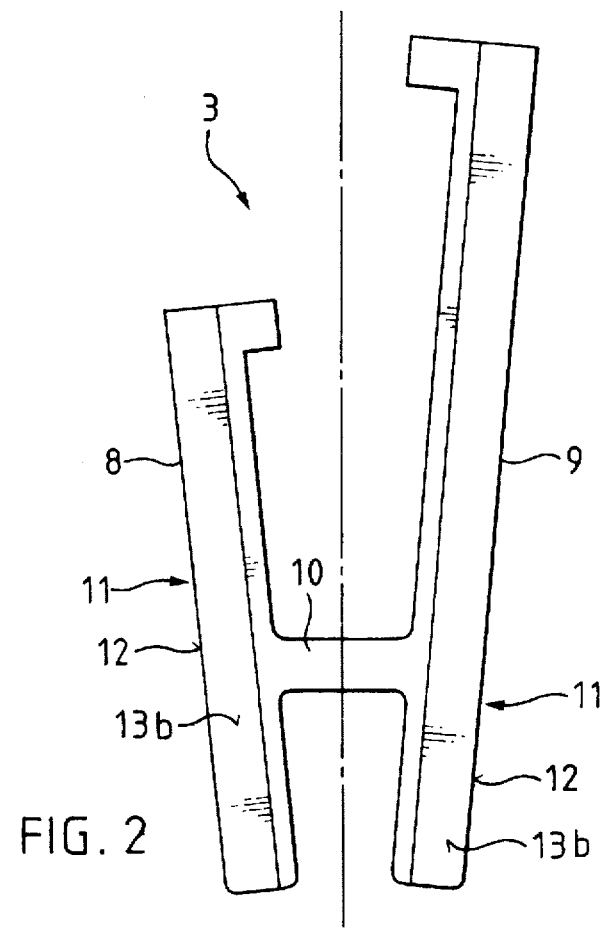
FIG. 2 shows a side view of a fastening element.

A model baseplate 1 (FIG. 1) has cutouts 2, arranged along a line following the course of a human maxillary arch, to receive fastening elements 3, as are illustrated in FIG. 2. The model baseplate 1 preferably consists of plastic, e.g. PETP and may be glass fibre-reinforced to increase the rigidity. The continuous cutouts 2 widen from the bottom towards the top transversely to the above-mentioned line so that mutually opposite bearing regions 4 (FIG. 4) extend away from one another towards the upper side of the model baseplate 1. They enclose an angle of about 10°. Each of the bearing regions 4 is formed by a planar rear wall 5 which is inclined slightly outward and by planar bearing faces 6a, 6b which, adjoining the said rear wall on both sides, are inclined slightly outward, and extend away from one another slightly towards the center of the cutout 2. The bearing region 4 thus forms a recess of trapezoidal cross-section which is constant over its length.

The cutouts 2 are usually closed by stoppers 7, for example made of a soft plastic material, e.g. foam material, which stoppers prevent molding compound penetrating into empty cutouts 2 and are pushed downwards when a fastening element 3 is inserted. Alternatively, a curved groove may be provided, which is recessed into the upper side of the model baseplate 1, connects the cutouts 2, and in which a strip of soft material is placed for the same purpose.

A differing embodiment of the model baseplate is also possible, in which the cutouts are connected by a curved opening, so that they only form pairs of mutually opposite, recess-like depressions in the side walls. However, a design of this type is already less favorable in terms of its strength than that described above.

The one-piece fastening element 3 has two essentially rigid limbs lying in one plane, a shorter limb 8 and a longer limb 9, which limbs are connected by an intermediate piece 10. The intermediate piece 10 has a rectangular cross-section and engages on each of the limbs 8, 9 at an attachment point which is located at a distance from the ends of the said limbs.

Apart from the difference in length of the sections of the limbs 8, 9 located above the intermediate piece 10, the fastening element 3 is of symmetrical design with regard to a center-plane intersecting the intermediate piece 10. In particular, the distance of the attachment point from the lower end is of equal size in both limbs, in the shorter limb it corresponds to about a third of the overall length and in the longer limb about a quarter. At the upper ends, both limbs are bent inward by about 90° in a hook-like manner.

The intermediate piece 10 can be bent slightly elastically, but is essentially unchangeable in the length, such that it forms a pivot about which the limbs 8, 9 can be elastically pivoted slightly towards one another, while the distance between the attachment points of the intermediate piece 10 on the limbs 8, 9 is virtually unchangeable. In the basic position, i.e. without elastic deformation of the intermediate piece 10, the limbs 8, 9 extend away from one another from the bottom towards the top. They enclose an angle of about 10°.

On the outer side, each of the limbs 8, 9 has a contact region 11 of approximately trapezoidal cross-section which is constant over the length of the limb, with a planar rear surface 12 and planar contact faces 13a, b which adjoin the said rear face on both sides and extend slightly away from one another towards the center of the fastening element 3.

The material of the fastening element 3 should have a high modulus of elasticity so that, despite the comparatively low geometrical moments of inertia, the limbs 8, 9 are virtually rigid, and the intermediate piece 10 having the smaller cross-section also opposes elastic deformations with a comparatively high resistance. Stainless steel in accordance with DIN 1.4305, for example, is very suitable.

If the fastening element 3 is now inserted into one of the cutouts 2 (FIGS. 3–5), the lower ends of the limbs 8, 9 do not quite reach the lower end of the cutout. The intermediate piece 10 lies approximately at half the height of the part of the fastening element 3 projecting into the cutout. In this case, its penetration into the cutout 2 is not limited by an actual depth stop, but by the cutout 2 tapering towards the bottom. Both the bearing regions 4 of the cutout 2 and the contact regions 11 of the fastening element 3 indeed extend away from one another slightly towards the top. In this case, the sections of the contact regions 11 located at the height of the intermediate piece 10, i.e. approximately at half height in the cutout 2, are held by the said intermediate piece at an essentially fixed distance which precisely fixes the vertical position of the fastening element 3. Additionally, the limbs 8, 9 can be pivoted slightly about the said sections so that they can adapt to the cutout 2 during insertion to compensate for manufacturing tolerances in such a way that their contact regions 11 lie snugly against the bearing regions 4 of the cutout 2 over its entire length.

The contact regions 11 are matched to the bearing regions 4 in such a way that (FIG. 5) the rear surface 12 does not lie against the rear wall 5, but, since it is slightly broader than the latter, is separated from it by a narrow gap. The stop is formed, on the one hand, by the bearing faces 6a, b and, on the other hand, by the contact faces 13a, b which respectively extend away from one another slightly both from the bottom towards the top and from the outside towards the inside. In this manner, the fastening element 3 is securely fixed vertically and laterally. It is in contact with the wall of the cutout 2 over a comparatively large area so that no high surface pressure occurs and material deformations remain correspondingly low.

The angle between the contact regions 11 of the two limbs 8, 9 of the fastening element 3 and the angle, corresponding to the former angle, between the bearing regions 4 of the cutout 2 and the angle between the contact faces 13a, b of each contact region 11 and the corresponding angle between the bearing faces 6a, b of each bearing region 4 are matched to the coefficient of friction between the fastening element 3 and the model baseplate 1 in such a way that, both in the vertical direction and inward towards the center of the cutout 2, there is slight self-locking. This improves the secure fit with which the fastening element 3 is held firmly in the cutout 2 without making insertion and removal of the said fastening element more difficult. The first-mentioned of the said angles, which is about 10° in the exemplary embodiment, as mentioned, is >0° and may lie, in particular, between 2° and 90°, preferably between 5° and 60°.

Figure 6:
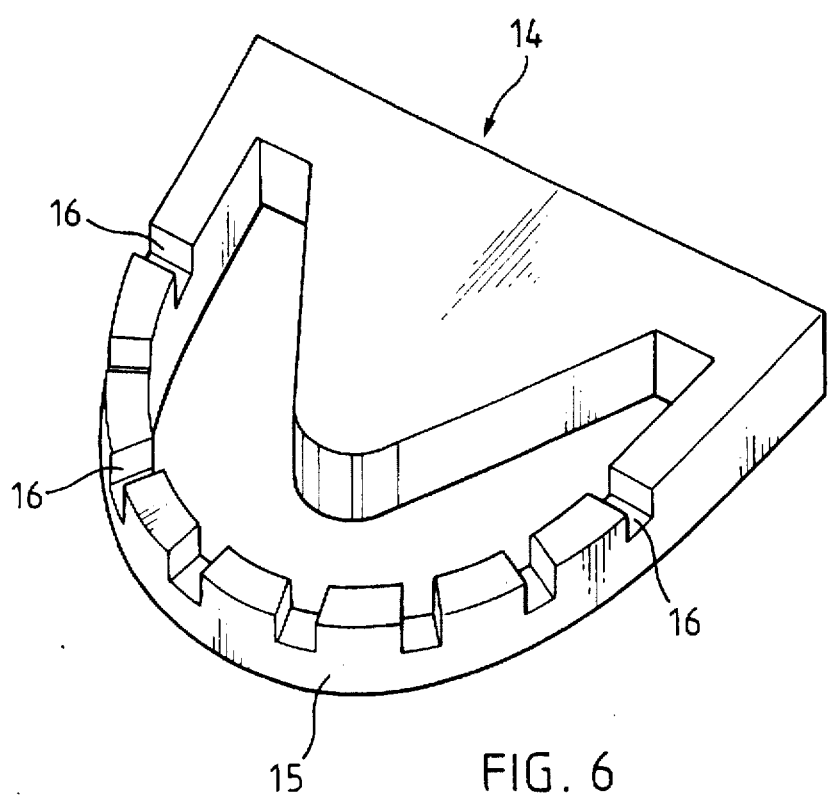
FIG. 6 shows a positioning plate.

A positioning plate 14 (FIG. 6) corresponds in its dimensions to the model baseplate 1. It has a bow 15 which follows the line along which the cutouts 2 are arranged and bears notches 16 arranged on the upper side corresponding to the positions of the cutouts 2.

To produce a dental model, an impression of a jaw or part of a jaw is produced from a silicone compound in the mouth of the patient and is placed on a baseplate. The positioning plate 14 is arranged above the impression. Fastening elements 3 are now fitted onto the said positioning plate in such a way that their intermediate pieces 10 come to rest in notches 16, and the upper end of the longer limb 9 points respectively downwards to the center of the tooth impression. In this case, depending on the size of the jaw and position of the tooth, the longer limb 9 may lie against the inner side or against the outer side of the bow 15.

Subsequently, the model baseplate I is fitted onto the positioning plate 14 with the upper side towards the bottom, the two plates are removed together and turned and, finally, the fastening elements 3 are transferred to the model baseplate 1, maintaining their relative positions, in that each individual one is pushed by means of a pin-like inserter into a cutout 2 in the said baseplate corresponding to its position. To improve the adherence of the fastening element 3 in the model baseplate 1, the former or even the latter may be heated beforehand to a forming temperature of the model baseplate 1. Finally, the positioning plate 14 is removed.

The impression is now filled with a molding compound such as a plaster compound and the model baseplate I is turned over again and pressed onto the plaster compound so that both limbs 8, 9 of each fastening element 3 are respectively embedded with their upper end regions in the said plaster compound. The stoppers 7 prevent plaster compound penetrating into empty cutouts 2. The cutouts 2 bearing fastening elements 3 are almost completely closed by the latter so that no plaster compound can penetrate further here either. Subsequently, the plaster compound is hardened.

Figure 3:
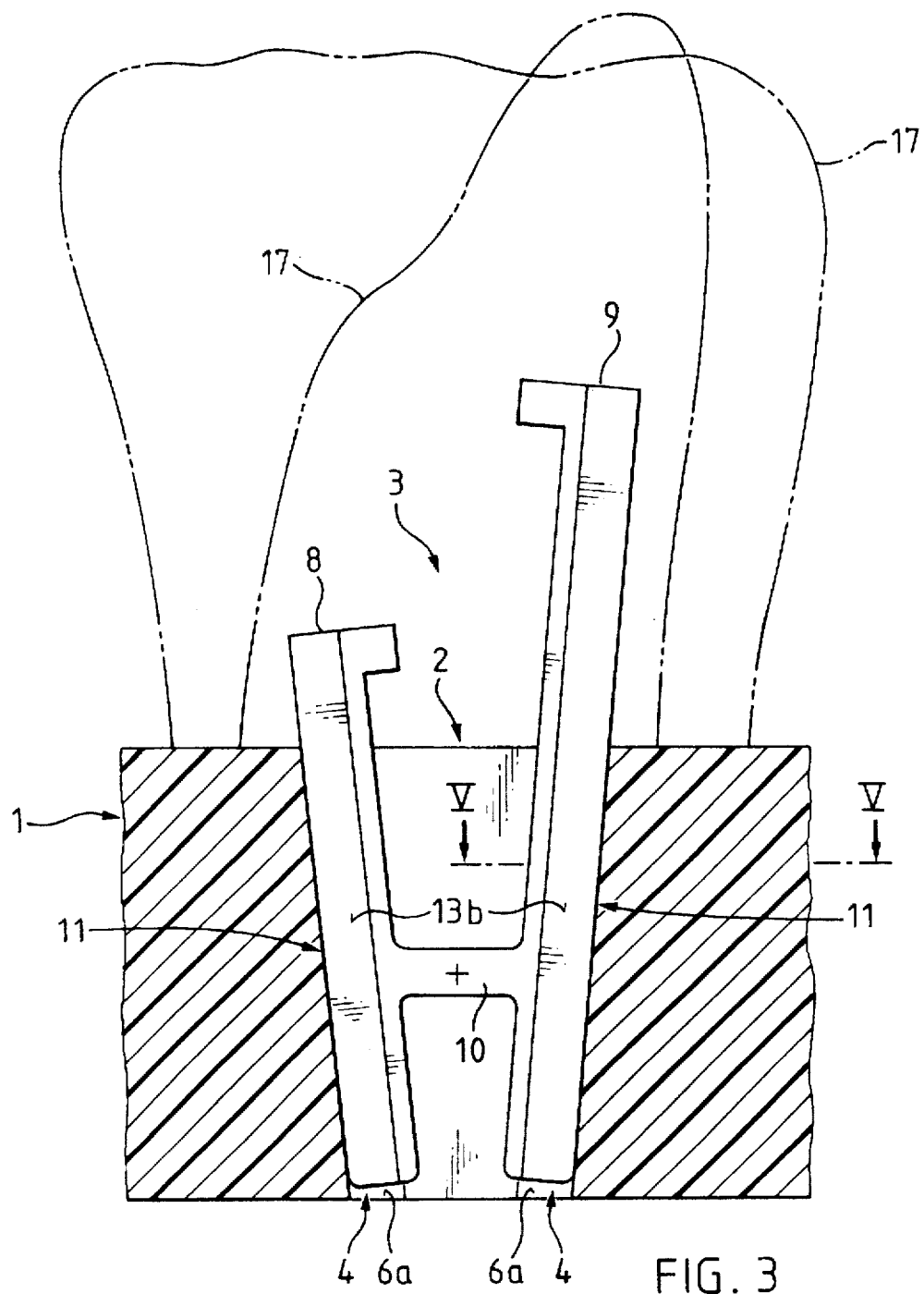
FIG. 3 shows a section through a part of a model baseplate with an inserted fastening element.
Figure 4:
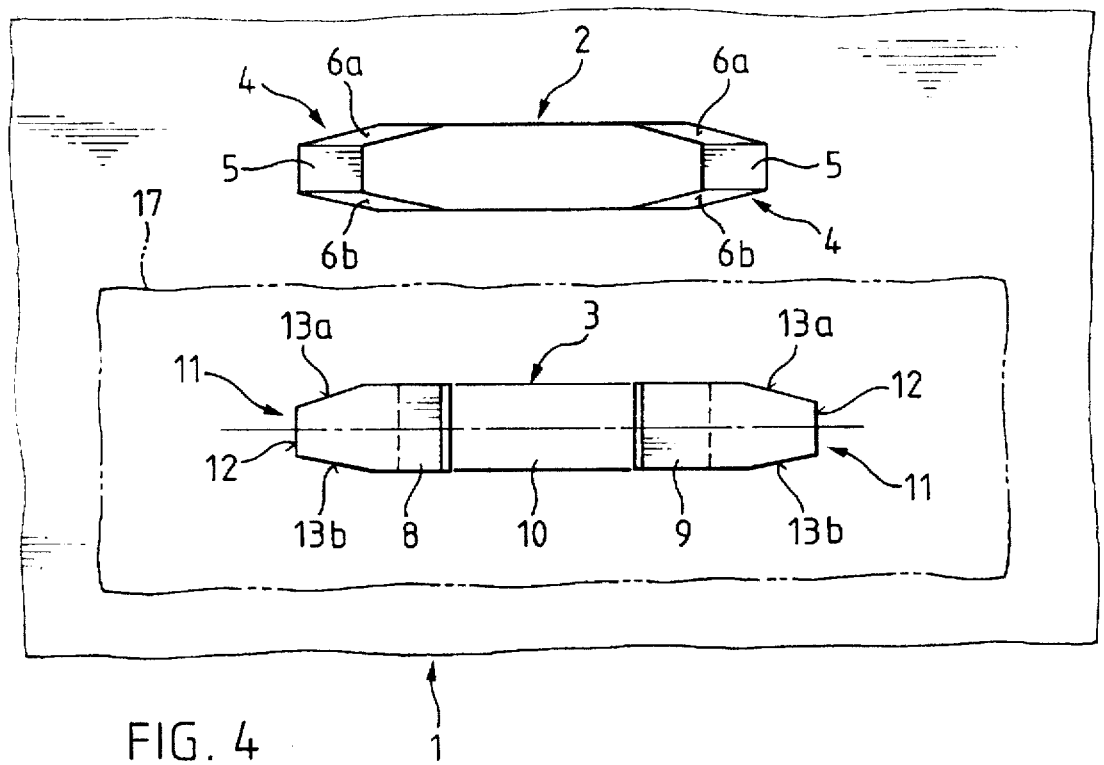
FIG. 4 shows a plan view of a detail of the model baseplate with an inserted fastening element.
Figure 5:
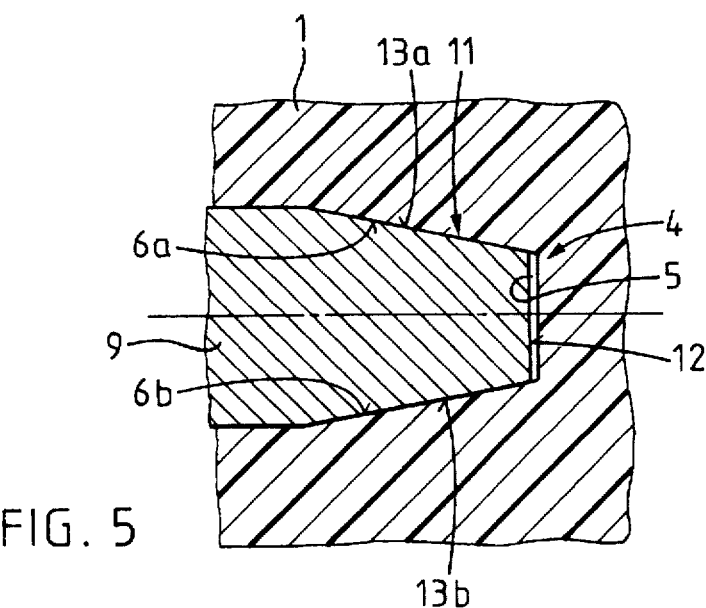
FIG. 5 shows, on an enlarged scale, a section along V—V in FIG. 3.

The working model thus formed is released from the impression and, finally, by hitting it lightly, also from the model baseplate 1. The limbs 8, 9 of each fastening element 3 are embedded so far into the working model that they are fixed non-pivotally in their mutual position. The working model can now be sawn up in such a way that each part contains at least one fastening element 3. In particular, each fastening element can bear a tooth model 17 (FIGS. 3, 4). The parts can be processed individually and, on account of the fastening elements 3, can be inserted into the model baseplate I again very precisely.

It will be apparent to those skilled in the art that various modifications and variations can be made in the disclosed process and product without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of producing a dental working model, in which an impression of a jaw or part of a jaw is made, comprising:

filling an impression with molding compound;

arranging fastening elements to be removable in a model baseplate;

pressing the model baseplate onto the molding compound so that the fastening elements respectively penetrate at least partially into the molding compound;

hardening the molding compound to fix the position of each fastening element and form a working model;

separating the working model from the impression and releasing the working model from the model baseplate; wherein the fastening elements respectively comprise at least two parts which are connected to each other by an intermediate piece and are movable relative to one another, and in that both parts of each fastening element are embedded so far in the molding compound that their mutual position is fixed after hardening of the molding compound.

2. The method according to claim 1, including arranging a positioning plate above the impression;

fitting the fastening elements onto the upper side of the positioning plate;

fitting the positioning plate together with the model baseplate in such a way that the upper side of the model baseplate faces the positioning plate; and transferring the fastening elements to the model baseplate while maintaining their relative positions.

3. The method according to claim 2, including individually pressing the fastening elements onto the model baseplate.

4. A dental fastening element for producing a dental working model, comprising:

two limbs which are connected to one another by an intermediate piece engaging on each limb intermediately between two free ends of the limb, each limb having a contact region on its outer side facing away from the other limb configured for engaging a dental model baseplate, the limbs being moveable relative to one another in such a way that the mutual position of their contact regions is adjustable.

5. The fastening element according to claim 4, wherein the limbs lie in one plane and enclose an angle >0° so that they extend away from one another, starting from lower ends where their distance is at a minimum.

6. The fastening element according to claim 5, wherein the angle enclosed by the limbs is between 2° and 90°.

7. The fastening element according to claim 6, wherein the angle enclosed by the limbs is between 5° and 60°.

8. The fastening element according to 5, wherein the intermediate piece engages nearer to the lower ends of the limbs.

9. The fastening element according to claim 4, wherein the limbs are of unequal length.

10. The fastening element according to claim 4, wherein the lower sections of the limbs located in each case between the lower end and the intermediate piece are of approximately equal length.

11. The fastening element according to claim 4, wherein at least one of the limbs is designed in a hook-like manner in the region of its upper end.

12. A dental fastening element having two limbs which are connected to one another by an intermediate piece engaging on each limb intermediately between two free ends of the limb, each limb having a contact region on its outer side facing away from the other limb, the limbs being moveable relative to one another in such a way that the mutual position of their contact regions is adjustable, wherein the limbs are rigid, the connection between the limbs is elastic, and the ends of the limbs are spaced apart from one another when the fastening element is in an unstressed condition.

13. A dental fastening element having two limbs which are connected to one another by an intermediate piece engaging on each limb intermediately between two free ends of the limb, each limb having a contact region on its outer side facing away from the other limb, the limbs being moveable relative to one another in such a way that the mutual position of their contact regions is adjustable, wherein, in at least one of the limbs, the contact region comprises two lateral contact faces which extend away from one another towards the inside.

14. A model baseplate comprising: a number of cutouts which are arranged along a line following a human maxillary arch or a part thereof, two bearing regions located opposite one another transversely to the said line being provided in each cutout, wherein at least one bearing region is bounded laterally by two bearing faces which extend away from one another towards the center of the cutout; and the opposite bearing regions extend away from one another from an underside of the model baseplate towards an upper side thereof.

15. The model baseplate according to claim 14, wherein the cutouts are designed to be at least partially continuous down to the underside of the model baseplate.

16. Model baseplate according to claim 15, wherein the cutouts are covered.

17. Model baseplate according to claim 15, wherein the cutouts are closed by removable stoppers.

18. A positioning plate comprising a single-walled bow following the line of a human maxillary arch or a part thereof, said bow having consecutive, continuous, transverse notches on its upper side extending through a thickness of the wall, each notch being configured to receive a dental fastening element.

19. A fastening system for producing a dental working model, having a model baseplate comprising a number of cutouts which are arranged along a line following a human maxillary arch or a part thereof, two bearing regions located opposite one another transversely to the said line being provided in each cutout, wherein at least one bearing region is bounded laterally by two bearing faces which extend away from one another towards the center of the cutout and at least one fastening element having two limbs which are connected to one another by an intermediate piece engaging on each limb intermediately between two free ends of the same, each limb having a contact region on its outer side facing away from the other limb, and the limbs are movable relative to one another in such a way that the mutual position of their contact regions is adjustable, for releasable insertion into a cutout in the model baseplate, the intermediate piece being located approximately at half the height of that part of the fastening element projecting into the model baseplate when the fastening element is inserted into the model baseplate.

20. A fastening system for producing a dental working model having a model baseplate comprising a number of cutouts which are arranged along a line following a human maxillary arch or a part thereof; two bearing regions located opposite one another transversely to the said line being provided in each cutout, wherein at least one bearing region is bounded laterally by two bearing faces which extend away from one another towards the center of the cutout;

wherein the opposite bearing regions extend away from one another from an underside of the model baseplate towards an upper side thereof and at least one fastening element having two limbs which are connected to one another by an intermediate piece engaging on each limb intermediately between two free ends of the same, each limb having a contact region on its outer side facing away from the other limb, and the limbs are movable relative to one another in such a way that the mutual position Of their contact regions is adjustable, and the limbs lie in one plane and enclose an angle >0° so that they extend away from one another, starting from lower ends where their distance is at a minimum for releasable insertion into a cutout in the model baseplate, wherein the angle between the limbs of the fastening element and the angle between the bearing regions of the cutout correspond to one another.

21. A fastening system for producing a dental working model having a model baseplate comprising a number of cutouts which are arranged along a line following a human maxillary, arch or a part thereof, two bearing regions located opposite one another transversely to the said line being provided in each cutout, wherein at least one bearing region is bounded laterally by two bearing faces which extend away from one another towards the center of the cutout;

wherein the opposite bearing regions extend away from one another from an underside of the model baseplate towards an upper side thereof and at least one fastening element for releasable insertion into the model baseplate, wherein said fastening element has two limbs which are connected to one another by an intermediate piece engaging on each limb intermediately between two free ends of the same, each limb having a contact region on its outer side facing away from the other limb, and the limbs are movable relative to one another in such a way that the mutual position of their contact regions is adjustable and in at least one of the limbs, the contact region comprising two lateral contact faces which extend away from one another towards the inside and the mutual position of bearing faces of a bearing region and the mutual position of the contact faces of a limb respectively correspond to one another.

22. The fastening system according to claim 21, wherein the angle between the bearing faces is matched to the coefficient of friction between the materials of the model baseplate and of the fastening element in such a way that self-locking occurs.

23. A fastening system to produce a dental working model having a model baseplate comprising a number of cutouts which are arranged along a line following a human maxillary arch or a part thereof and at least one fastening element having two limbs which are connected to one another, the connection between the limbs being produced by at least one intermediate piece which engages on each of the limbs between the free ends thereof, and is designed in such a way that the limbs can be moved relative to one another to adjust the mutual position of their contact regions, and having a positioning plate comprising a bow following the line of a human maxillary arch or a part thereof, which bow has consecutive notches on its upper side, the positions of the notches on the bow of the positioning plate corresponding to those of the cutouts in the model baseplate.

24. The fastening system of claim 23, wherein the cutouts include two bearing regions located opposite one another transversely to the said line being provided in each cutout, wherein at least one bearing region is bounded laterally by two bearing faces which extend away from one another towards the center of the cutout, and the opposite bearing regions extend away from one another from an underside of the model baseplate towards an upper side thereof.

25. The fastening system of claim 23, wherein each limb of the fastening elements has a contact region on its outer side facing away from the other limb, and the limbs lie in one plane and enclose an angle >0° so that they extend away from one another, starting from lower ends where their distance is at a minimum for releasable insertion into a cutout in the model baseplate.

* * * * *

UNITED STATES PATENT AND TRADEMARK OFFICE
CERTIFICATE OF CORRECTION

PATENT NO.   : 5,738,518
DATED        : April 14, 1998
INVENTOR     : Claude NOWAK It is certified that error appears in the above-identified patent and that said Letters Patent is hereby corrected as shown below:

Claim 20, col. 8, line 16, "Of " should read --of--.

Claim 21, col. 8, line 26, "maxillary, arch" should read --maxillary arch--.

Signed and Sealed this

Sixth Day of October, 1998

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,738,518
DATED : April 14, 1998
INVENTOR(S) : Claude NOWAK

It is certified that error appears in the above-indentified patent and that said Letters Patent is hereby corrected as shown below:

Title page, col. 1, delete item [76] in its entirety and substitute therefor
--[75] Inventor: Claude Nowak, Wettingen, Switzerland
[73] Assignee: Mikrona Technologie AG, Spreitenbach, Switzerland--.

Title page, col. 2, below "Primary Examiner - Cary E. O'Connor", insert
--Attorney, Agent or Firm - Finnegan, Henderson, Farabow, Garrett & Dunner, L.L.P.--

Signed and Sealed this

Twenty-sixth Day of October, 1999

Attest:

Q. TODD DICKINSON

*Attesting Officer*        *Acting Commissioner of Patents and Trademarks*